United States Patent [19]

Matvias

[11] 4,375,220
[45] Mar. 1, 1983

[54] MICROWAVE APPLICATOR WITH COOLING MECHANISM FOR INTRACAVITARY TREATMENT OF CANCER

[76] Inventor: Fredrick M. Matvias, 405 McKinley, Grosse Pointe Farms, Mich. 48236

[21] Appl. No.: 148,528

[22] Filed: May 9, 1980

[51] Int. Cl.³ .............................................. A61N 1/40
[52] U.S. Cl. .................................... 128/804; 128/401
[58] Field of Search ....................... 128/653, 399–401, 128/804

[56] References Cited

U.S. PATENT DOCUMENTS

| | | | |
|---|---|---|---|
| 2,407,690 | 9/1946 | Southworth | 128/804 |
| 3,494,723 | 2/1970 | Gray | 219/10.55 R |
| 4,140,130 | 2/1979 | Storm | 128/804 X |
| 4,162,500 | 7/1979 | Jacobi et al. | 128/653 |

FOREIGN PATENT DOCUMENTS

| | | | |
|---|---|---|---|
| 2407559 | 8/1975 | Fed. Rep. of Germany | 128/804 |
| 862646 | 3/1961 | United Kingdom | 128/804 |

*Primary Examiner*—Kyle L. Howell
*Assistant Examiner*—Francis J. Jaworski
*Attorney, Agent, or Firm*—Charles W. Chandler

[57] ABSTRACT

Microwave applicator with cooling mechanism for intracavitary treatment of cancer comprises a jacket with means for delivering water, air or a combination of water and air into the jacket to control the external and internal jacket temperature and temperature of surrounding tissues.

14 Claims, 9 Drawing Figures

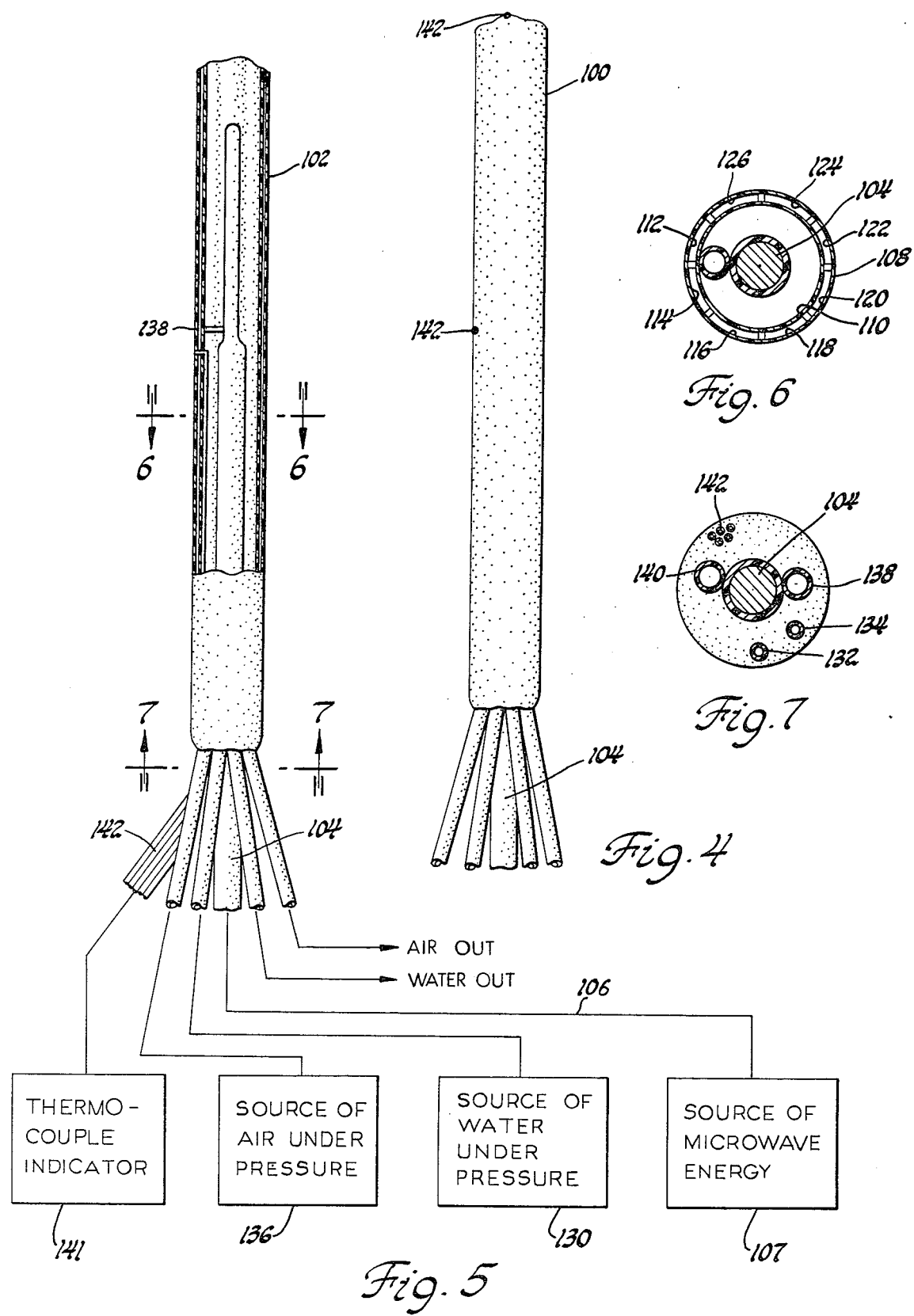

MICROWAVE APPLICATOR WITH COOLING MECHANISM FOR INTRACAVITARY TREATMENT OF CANCER

BACKGROUND OF THE INVENTION

Hyperthermia is a technique for treating cancerous tissue cells involving the application of heat in the vicinity of the cancer cells. The cancer is selectively destroyed after several treatments. This technique has been successfully employed for cancers that can be externally treated.

However, some cancers are located such that they cannot be successfully treated with conventional external techniques. For example, certain lung cancers are too remote from the radiation to be successfully treated by a microwave electrode located adjacent the skin of the user. The heat generated by the electrode is such that it destroys noncancerous tissue if left in contact with such tissues for a sufficient time to affect cancerous tissue. Heretofore, water has not been suitable as a cooling medium because microwave energy can be absorbed by a water shield greater than about one millimeter thick.

SUMMARY OF THE INVENTION

The broad purpose of the present invention is to provide a microwave applicator having means for controlling the heat generated by internally applied microwave energy for treating cancerous tissues. In the preferred embodiment of the invention, the microwave antenna is housed in a jacket having a diameter suited for the particular body opening through which it is to be inserted. The jacket is preferably formed of a flexible silicone or resin. A flexible silicone jacket has been introduced through the esophagus into the mediastinum for treatment of lung and chest tumors.

In one form of the invention, the jacket has longitudinal cooling chambers forming a shield around the antenna for receiving water in a counter-current flow. The chambers, no more than one millimeter in thickness, are used to control the heat generated by the electrode. Thermocouples are mounted along the jacket for monitoring the temperature in the event that it may exceed 43° C.

In another form of the invention, the electrode is housed in a short perforated jacket adapted for treating cancer of the nasopharynx, oral pharynx, and throat. A mouthpiece is attached to one end of the jacket which the patient bites with his teeth to precisely locate the antenna for each treatment.

Still another embodiment of the invention contemplates an elongated jacket having both counter-current water chambers for cooling, as well as air tubes which deliver air along the electrode to control the jacket temperature.

Still other objects and advantages of the invention will become readily apparent to those skilled in the art to which the invention pertains upon reference to the following detailed description.

DESCRIPTION OF THE DRAWINGS

The description refers to the accompanying drawings in which like reference characters refer to like parts throughout the several views, and in which:

FIG. 4 is a view of another embodiment of a water-cooled embodiment of the invention;

FIG. 5 is a sectional view of the embodiment of FIG. 4;

FIG. 6 is a view as taken along lines 6—6 of FIG. 5;

FIG. 7 is a view as taken along lines 7—7 of FIG. 5;

DESCRIPTION OF THE PREFERRED EMBODIMENT

Figure 1:
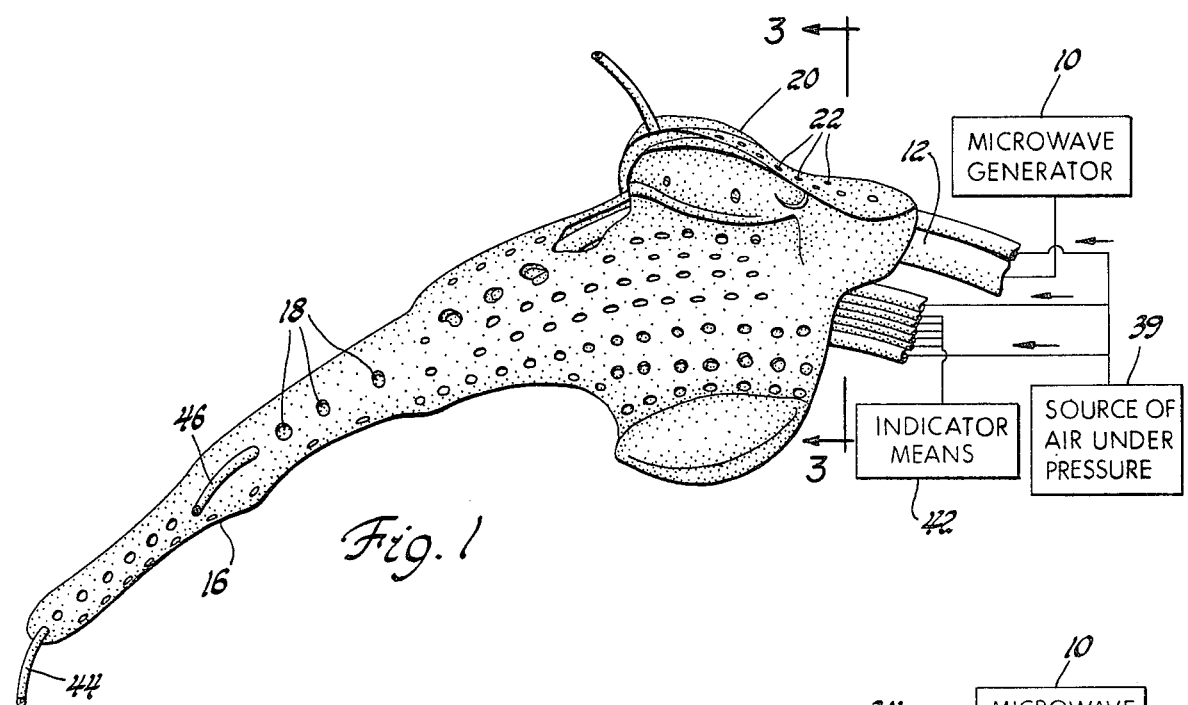
FIG. 1 is a view of an air-cooled microwave applicator illustrating the preferred embodiment of the invention.

Referring to FIG. 1, a microwave generator 10 is connected to an elongated coaxial cable 12 having an electrode having its end shaped in the form of a dipole antenna 14. Such antennas are well known to those skilled in the art and are normally used in localized hyperthermia treatment in which the temperature of a cancer tumor is raised to approximately 42.5° C. to 43.5° C. for one half to one hour at a time. Higher internal temperatures can be achieved. Normal body temperature is approximately 37° C. The power required to accomplish the degree of heating depends upon the size and type of tumor, its location, the healthy tissues surrounding it, and the like.

A hollow flexible jacket 16 is mounted on the outer end of antenna 14. Jacket 16 is flexible to accomodate the shape of the user's throat. Jacket 16 has a plurality of air openings 18 along its length.

A mouthpiece 20 of a stiffer plastic is attached to jacket 16, and has a plurality of openings 22 for discharging air.

Figure 3:
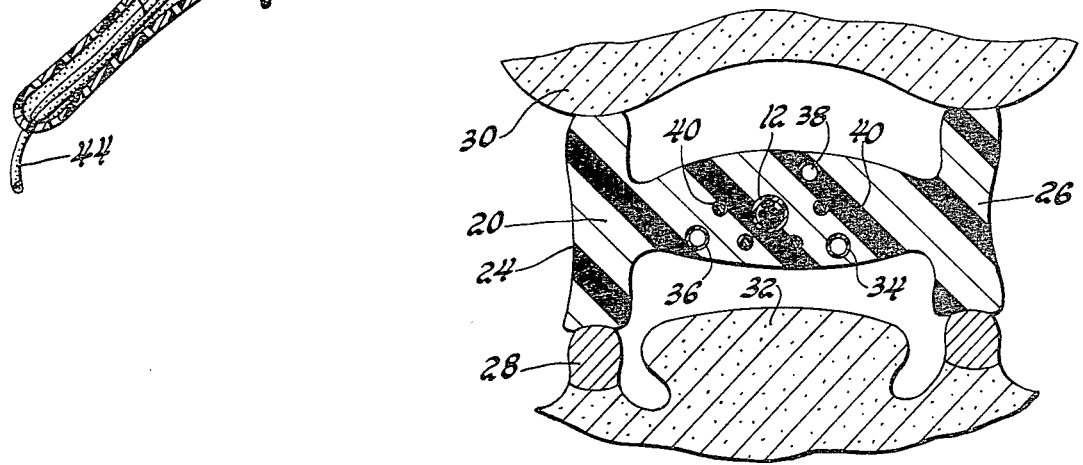
FIG. 3 is a view as seen along lines 3—3 of FIG. 1.

Referring to FIG. 3, the mouthpiece has a pair of biting sections 24 and 26 adapted to be disposed between lower jaws 28 and upper jaws 30 of the user to position the mouthpiece and jacket above the user's tongue 32.

Figure 2:
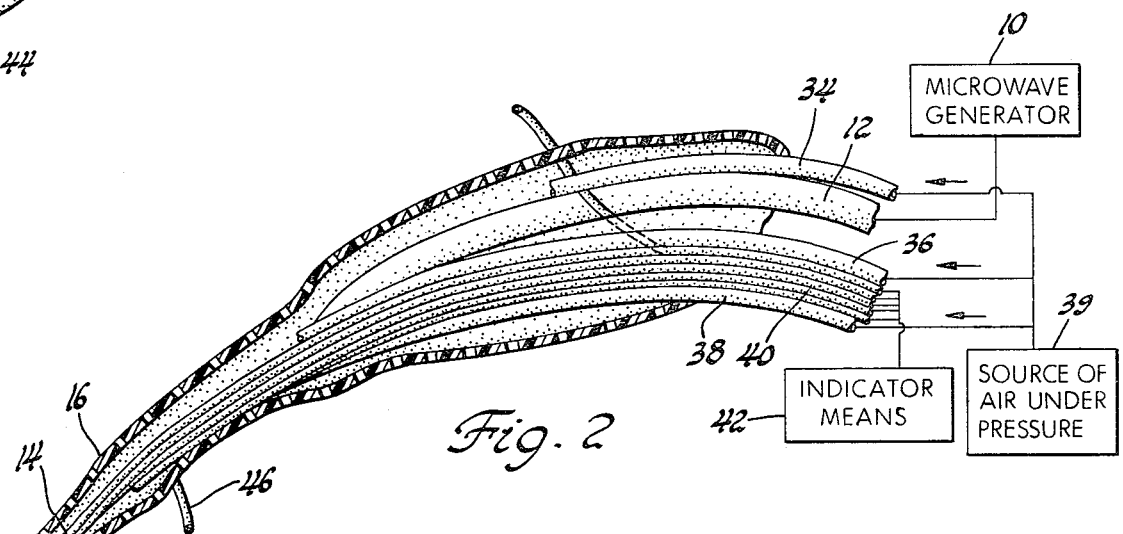
FIG. 2 is a longitudinal sectional view through the embodiment of FIG. 1, parts of the apparatus being illustrated schematically.

Three air tubes 34, 36, and 38 are disposed in the jacket as illustrated in FIG. 2. A source of air under pressure is connected to the inlet ends of the air tubes. The outlet ends of the air tubes are disposed either within the mouthpiece or the jacket as illustrated. The air received from source 39 passes along the length of the antenna to control the temperature of the jacket and the mouthpiece and then passes outwardly through openings 18 and 20 to cool the surface tissues.

A plurality of thermocouple leads 40, connected to indicator means 42, are disposed along the length of the jacket, as at 44 and 46, so that the operator can monitor the temperature of the jacket during treatment. If it rises to a temperature higher than 43° C., the device can be removed from the user's mouth.

In use, the jacket is inserted in the user's throat and located in position by the user biting down on the biting sections 24 and 26. The mouthpiece precisely locates the antenna for each treatment and prevents the patient from gagging.

Referring to FIGS. 4 to 7, another microwave apparatus 100 comprises an elongated jacket 102 mounted on the end of an electrode 104. In this embodiment of the invention, the electrode is connected through cable means 106 to a source of microwave energy 107.

Jacket 102 is also formed of a relatively flexible silicone plastic, and is intended to be inserted into body cavities where air cooling is not suitable.

Jacket 102 has a relatively thin outer wall 108 and inner wall means 110 forming a series of eight longitudinal chambers 112, 114, 116, 118, 120, 122, 124, and 126.

Each of the chambers runs substantially the full length of the jacket. Water is received from a source 130 into bottom inlet 132, up chamber 118, down chamber 120, up chamber 122, down chamber 124, up chamber 126, down chamber 112, up chamber 114, and down chamber 116 where it passes through bottom outlet 134. The water going up each vertical chamber passes in heat exchange relationship with the water in the neighboring chambers. The radial thickness of each chamber is about one millimeter. The width of each chamber is preferably about five millimeters.

This arrangement provides several advantages. The chamber thickness permits the water to be used for controlling the jacket temperature and temperature of surrounding tissues without significantly reducing the effectiveness of the microwave radiation. The chamber width is chosen to optimize the amount of water pressure necessary to move the water in the countercurrent flow in the jacket.

A source of air under pressure 136 delivers air through a tube 138 into the jacket where it passes upwardly along the electrode before being discharged through outlet 140.

Thermocouple indicator means 141 are connected to a series of thermocouples 142 which are connected along the length of the jacket so that the user can closely monitor the jacket temperature, remove it from the patient if a hot spot should occur and either increase or reduce the flow of water, and change the water temperature either higher or lower depending upon the temperature control desired. It is to be noted that the jacket is formed of a relatively thin plastic or silicone.

Figure 8:
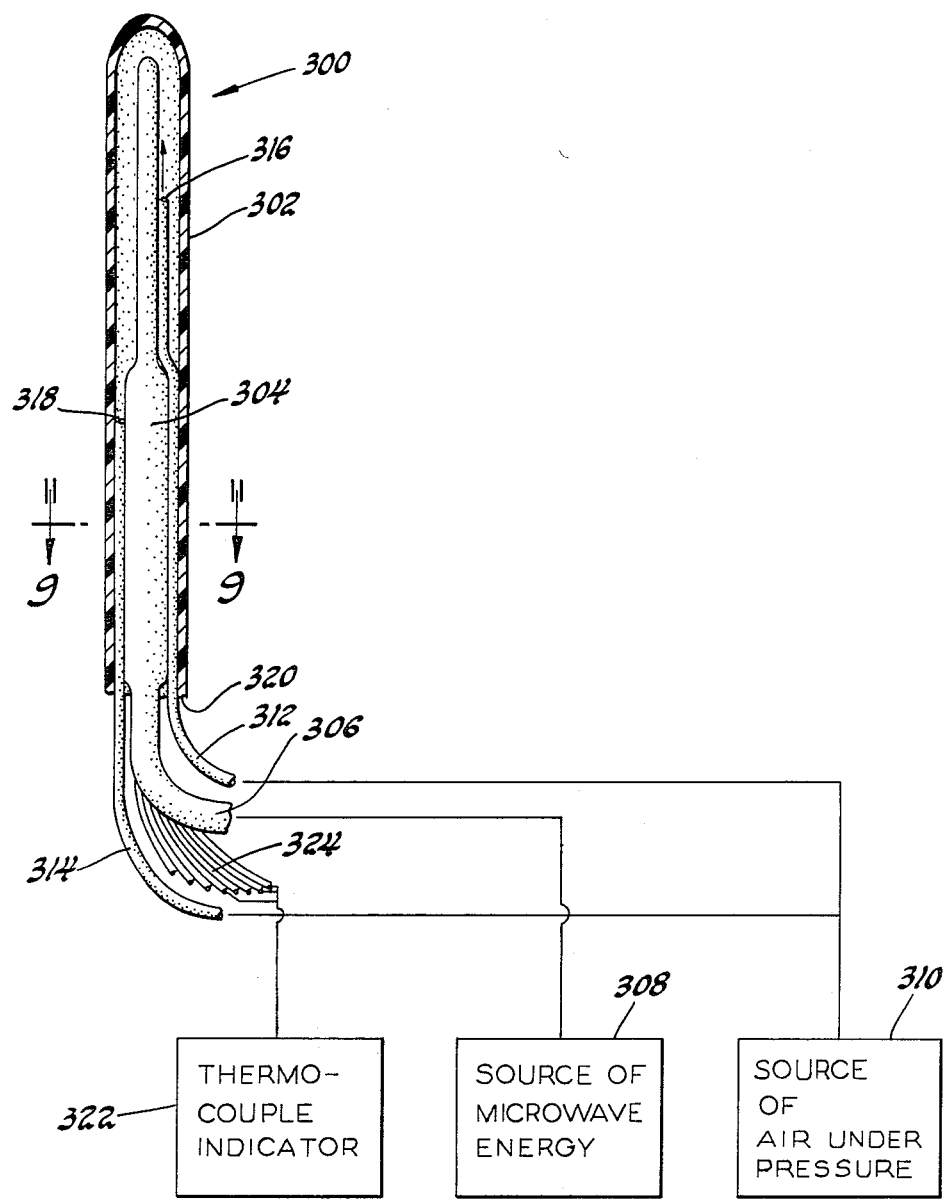
FIG. 8 is a longitudinal sectional view of still another embodiment of the invention.
Figure 9:
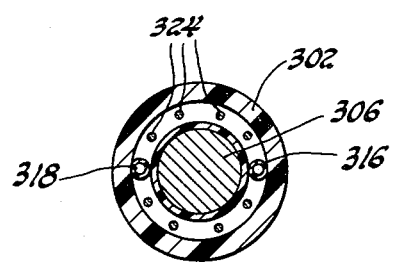
FIG. 9 is a view as seen along lines 9—9 of FIG. 8.

FIGS. 8 and 9 show another embodiment of the invention comprising a microwave apparatus 300. This embodiment has a jacket 302 preferably formed of a flexible plastic such as silicone. A microwave radiating antenna 304 is housed within jacket 302 and connected by cable 306 to a source of microwave energy 308. A source of air under pressure 310 is connected to a pair of inlet tubes 312 and 314. The upper end of tube 312 terminates at 316 and the upper end of tube 314 terminates at 318. The tubes direct the air toward the closed end of the jacket. The air then flows down toward the jacket's open end 320 and out of the jacket.

Thermocouple indicator means 322 are connected to a plurality of thermocouple leads 324 which have their sensing ends connected at various positions along the length of the jacket so that the user can closely monitor the surface temperature and either increase or reduce the air flow should a hot spot develop. This arrangement is particularly useful where the device is to treat cancer in the lungs or in the throat where the air must be exhausted through the jacket.

The invention contemplates other conductor means for delivering microwave energy to the jacket such as some form of housing which delivers the energy from a remotely located generator.

Having described my invention, I claim:

1. Apparatus adapted for insertion into a body opening for microwave energy to internally develop heat for the treatment of body tissue comprising:
    a source of microwave radiation;
    an elongated jacket suited for insertion in a body opening, and first means in said jacket for providing microwave energy from said source to generate heat in body tissue;
    means in said jacket forming at least one longitudinal chamber extending along said jacket having a thickness of about one millimeter in the direction of radiation; and
    a source of cooling fluid, and means for continuously delivering said fluid to said at least one chamber in a first direction along said jacket, and then in the opposite direction along said jacket to form a fluid shield along said jacket having a thickness of about one millimeter for controlling the heat generated on the external surface of the jacket.

2. Microwave apparatus as defined in claim 1, in which said source of radiation comprises an electrode.

3. Microwave apparatus as defined in claim 1, in which the cooling fluid comprises air.

4. Microwave apparatus as defined in claim 1, in which said cooling fluid comprises water.

5. Microwave apparatus as defined in claim 1, including thermocouple means mounted on the jacket for indicating the external temperature thereof, and means adapted for adjusting the flow of the cooling fluid through said jacket according to the temperature indicated by the thermocouple means.

6. Microwave apparatus as defined in claim 1, in which the cooling fluid comprises air and water.

7. Microwave apparatus as defined in claim 1, including means for delivering air into the jacket adjacent the first and second chambers.

8. Microwave apparatus as defined in claim 7, including thermocouple means mounted along said jacket, and means for adjusting the temperature of said jacket according to the indication of the thermocouple means.

9. Microwave apparatus as defined in claim 1, in which the jacket has an open end and a closed end, and including means for delivering said cooling fluid into selected positions in said jacket such that the fluid is discharged through said open end from the jacket.

10. Apparatus as defined in claim 1, in which said first means comprises an electrode having its end shaped to form an antenna, said antenna being disposed in said jacket and surrounded by the fluid shield.

11. Microwave apparatus as defined in claim 10, in which said at least one chamber comprises a plurality of elongated, longitudinal chambers collectively forming a shield about said source of microwave radiation.

12. Apparatus as defined in claim 1, in which said jacket is flexible so as to be suited for insertion in a selected opening in a human body.

13. Apparatus for treating cancerous tissue in a human body comprising:
    an electrode having its end shaped to form an antenna, and means connected to the electrode operative to generate microwave energy which radiates from said antenna;
    an elongated flexible jacket adapted for insertion in a body opening, the jacket having a plurality of longitudinal chambers about the jacket;
    a source of a liquid, and means for deliverying the liquid to the longitudinal chambers to form a liquid shield having a thickness of about one millimeter in which the liquid passes alternately in a first longitudinal direction along the jacket and then the opposite longitudinal direction as the liquid progresses about the jacket for controlling the heat on the external surface thereof; and the antenna being disposed in the jacket such that microwave energy is radiated through the liquid shield so as to develop heat in the tissue surrounding the body opening.

14. Apparatus adapted for insertion into a body opening for microwave energy to internally develop heat for the treatment of body tissue comprising;

a source of microwave radiation;

an elongated jacket suited for insertion in a body opening, and first means in said jacket for providing microwave energy from said source to generate heat in body tissue;

means in said jacket forming a plurality of side-by-side elongated, longitudinal, chambers collectively forming a confinement for passing a liquid shield of about one millimeter thickness in the direction of radiation; and a source of cooling water and means for continuously delivering said water to said chambers in a first longitudinal direction along said jacket, and then in the opposite longitudinal direction along said jacket to form a liquid shield along said jacket having a thickness of about one millimeter in the path of radiation for controlling the heat generated on the external surface of the jacket.

* * * * *